(12) United States Patent
Quraishi et al.

(10) Patent No.: US 8,580,576 B2
(45) Date of Patent: Nov. 12, 2013

(54) METHOD FOR BODILY FLUID SAMPLE TRANSFER DURING ANALYTE DETERMINATION

(75) Inventors: Khalid R. Quraishi, Sunnyvale, CA (US); David Matzinger, Menlo Park, CA (US)

(73) Assignee: Cilag GmbH International, Zug (CH)

( * ) Notice: Subject to any disclaimer, the term of this patent is extended or adjusted under 35 U.S.C. 154(b) by 326 days.

(21) Appl. No.: 13/198,510

(22) Filed: Aug. 4, 2011

(65) Prior Publication Data

US 2013/0034870 A1  Feb. 7, 2013

(51) Int. Cl.
*G01N 1/10* (2006.01)

(52) U.S. Cl.
USPC .............. 436/180; 436/63; 436/174; 436/807

(58) Field of Classification Search
USPC .................................... 436/180, 63, 174, 807
See application file for complete search history.

(56) References Cited

U.S. PATENT DOCUMENTS

| | | | |
|---|---|---|---|
| 5,208,163 A * | 5/1993 | Charlton et al. ................. | 436/63 |
| 5,515,170 A | 5/1996 | Matzinger et al. | |
| 5,708,247 A | 1/1998 | McAleer et al. | |
| 5,919,711 A * | 7/1999 | Boyd et al. ..................... | 436/178 |
| 5,951,836 A | 9/1999 | McAleer et al. | |
| 5,968,836 A | 10/1999 | Matzinger et al. | |
| 6,241,862 B1 | 6/2001 | McAleer et al. | |
| 6,284,125 B1 | 9/2001 | Hodges et al. | |
| 6,488,827 B1 | 12/2002 | Shartle | |
| 6,884,592 B2 | 4/2005 | Matzinger et al. | |
| 7,131,342 B2 | 11/2006 | Hodges | |
| 7,182,910 B2 | 2/2007 | Allen et al. | |
| 7,195,704 B2 | 3/2007 | Kermani et al. | |
| 7,468,125 B2 | 12/2008 | Kraft et al. | |
| 7,655,120 B2 | 2/2010 | Bae et al. | |
| 7,695,676 B2 | 4/2010 | Kloepfer et al. | |
| 7,766,846 B2 | 8/2010 | Wong et al. | |
| 7,819,822 B2 | 10/2010 | Calasso et al. | |
| 7,875,047 B2 | 1/2011 | Freeman et al. | |
| 7,977,106 B2 | 7/2011 | Opalsky et al. | |
| 2007/0084734 A1 | 4/2007 | Roberts et al. | |
| 2007/0193882 A1 | 8/2007 | Dai et al. | |
| 2007/0263046 A1 | 11/2007 | Iwasa et al. | |
| 2009/0301899 A1 | 12/2009 | Hodges et al. | |
| 2010/0136566 A1 | 6/2010 | Mehra et al. | |
| 2011/0105951 A1 | 5/2011 | Bernstein et al. | |

FOREIGN PATENT DOCUMENTS

WO       WO 2004/063393       7/2004

* cited by examiner

*Primary Examiner* — Monique Cole

(57) ABSTRACT

A method for the transfer of a bodily fluid sample (such as a whole blood sample) during the determination of an analyte (e.g., glucose) in the bodily fluid sample includes applying the bodily fluid sample to a sample collection reservoir of an analytical test strip (for example, an electrochemical-based analytical test strip). During such application, the sample collection reservoir is isolated from fluid communication with a determination chamber of the analytical test strip. The analytical test strip is subsequently inserted into a test meter such that the sample collection reservoir is placed into fluid communication with the determination chamber and such that at least a portion of the bodily fluid sample is consequentially transferred from the sample collection reservoir to the determination chamber. The method further includes determining the analyte in the bodily fluid sample transferred to the determination chamber.

11 Claims, 6 Drawing Sheets

METHOD FOR BODILY FLUID SAMPLE TRANSFER DURING ANALYTE DETERMINATION

BACKGROUND OF THE INVENTION

1. Field of the Invention

The present invention relates, in general, to medical devices and methods, in particular, to medical devices and related methods.

2. Description of Related Art

The determination (e.g., detection and/or concentration measurement) of an analyte in a fluid sample is of particular interest in the medical field. For example, it can be desirable to determine glucose, ketone bodies, cholesterol, lipoproteins, triglycerides, acetaminophen and/or HbA1c concentrations in a sample of a bodily fluid such as urine, blood, plasma or interstitial fluid. Such determinations can be achieved using a test meter (such as a hand-held test meter) in combination with analytical test strips (e.g., electrochemical-based analytical test strips).

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements, of which:

DETAILED DESCRIPTION OF ILLUSTRATIVE EMBODIMENTS

Figure 1:
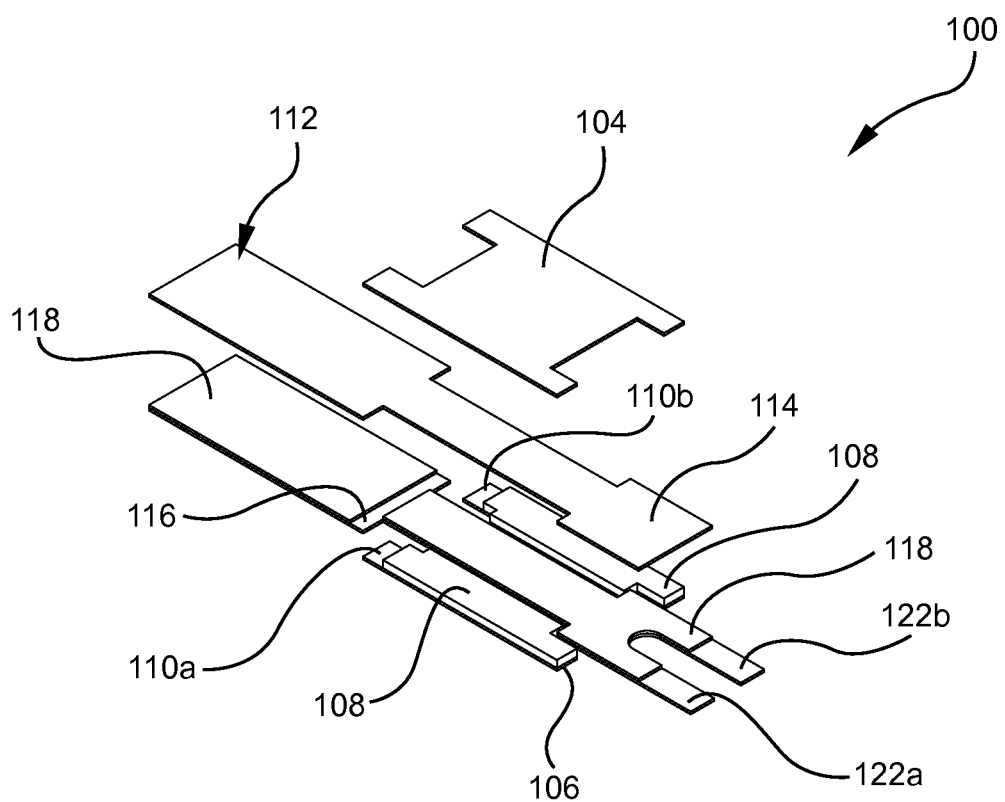
FIG. 1 is a simplified exploded view of an analytical test strip as can be employed in methods according to the present invention.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

In general, methods for the transfer of a bodily fluid sample (such as a whole blood sample) during the determination of an analyte (e.g., glucose) in the bodily fluid sample according to embodiments of the present invention include applying the bodily fluid sample to a sample collection reservoir of an analytical test strip (for example, an electrochemical-based analytical test strip). During such application, the sample collection reservoir is isolated from fluid communication with a determination chamber of the analytical test strip. The analytical test strip is subsequently inserted into a test meter such that the sample collection reservoir is placed into fluid communication with the determination chamber and such that at least a portion of the bodily fluid sample is consequentially (i.e., automatically) transferred from the sample collection reservoir to the determination chamber. The method further includes determining the analyte in the bodily fluid sample transferred to the determination chamber.

Methods according to embodiments of the present invention are beneficial in that they provide for a bodily fluid sample to be applied (i.e., "dosed") to the analytical test strip before the analytical test strip is inserted into the associated test meter. Such application is referred to as off-meter dosing and is beneficial in that a user need only handle the analytical test strip during application of the bodily fluid sample rather than handling a more bulky combination of test meter and inserted analytical test strip.

Moreover, in methods according to the present invention, the bodily fluid sample is not transferred to a determination chamber of the analytical test strip (and exposed to any reagents and/or electrodes contained therein) until the analytical test strip is inserted into the test meter. This feature of the method (and analytical test strips employed in the method) beneficially enables the test meter to conduct analytical measurements on a bodily fluid sample that has been present in the determination chamber and exposed to reagents therein for a relatively short duration. Such measurements provide for improved determination accuracy by occurring while diffusion and/or reaction of various analyte and reagent species are underway. For example, it can be beneficial to conduct measurements prior to reagent components diffusing to an electrode of the analytical test strip. However, such diffusion occurs relatively quickly and conducting measurements prior to such diffusion would be problematic if the bodily fluid sample was exposed to reagents in the determination chamber prior to insertion of the analytical test strip into the test meter. Methods according to embodiments of the present invention beneficially overcome such problems by transferring at least a portion of the bodily fluid sample into the determination chamber only upon insertion of the analytical test strip into the test meter and not prior thereto. Prior to such insertion, the bodily fluid sample is held in a sample collection reservoir that is not in fluid communication with the determination chamber.

Referring to FIGS. 1 through 8, an analytical test strip 100 that can be employed in methods according to embodiments of the present invention includes a sample collection portion 102 with a collection portion top layer 104 (not depicted in FIGS. 6A and 6B for clarity), a collection portion bottom layer 106, and a patterned collection layer spacer layer 108. Sample collection portion 102 is configured such that dual sample collection reservoirs 110a and 110b are defined (see FIG. 1 in particular). The presence of two (i.e., dual) sample collection reservoirs enables the application of a bodily fluid sample to analytical test strip 100 from either side of the analytical test strip.

Sample collection reservoirs 110a and 110b have at least one capillary dimension and, therefore, are considered capillary sample collection reservoirs. For example, in the embodiment and perspective of FIGS. 1-8, the dimensional height of the capillary sample collection reservoir is in the range of 0.15 mm to 0.5 mm.

Figure 6A:
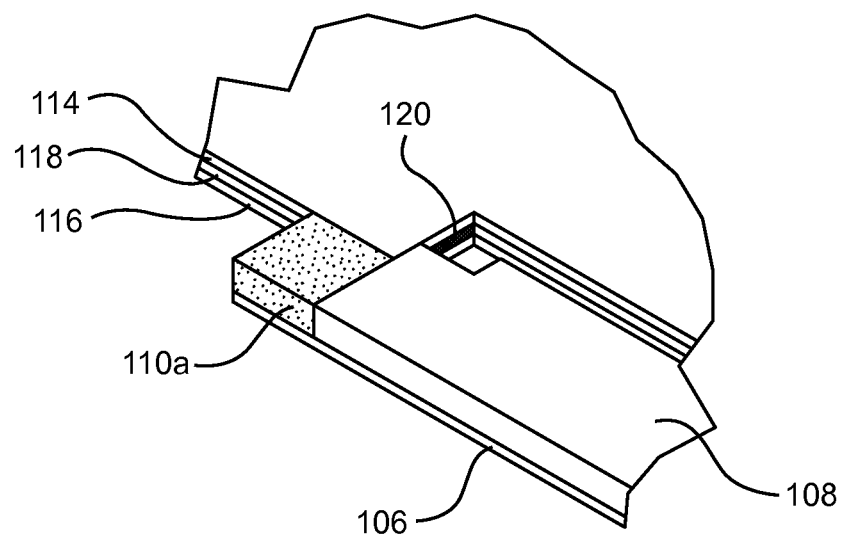
FIGS. 6A and 6B are simplified perspective depictions of a portion of the analytical test strip of FIG. 2 depicting the transfer of a bodily fluid sample (depicted by dotted areas) initially in the sample collection reservoir (FIG. 6A) into the determination chamber (FIG. 6B) after insertion of the analytical test strip into a test meter during a method according to the present invention.
Figure 6B:
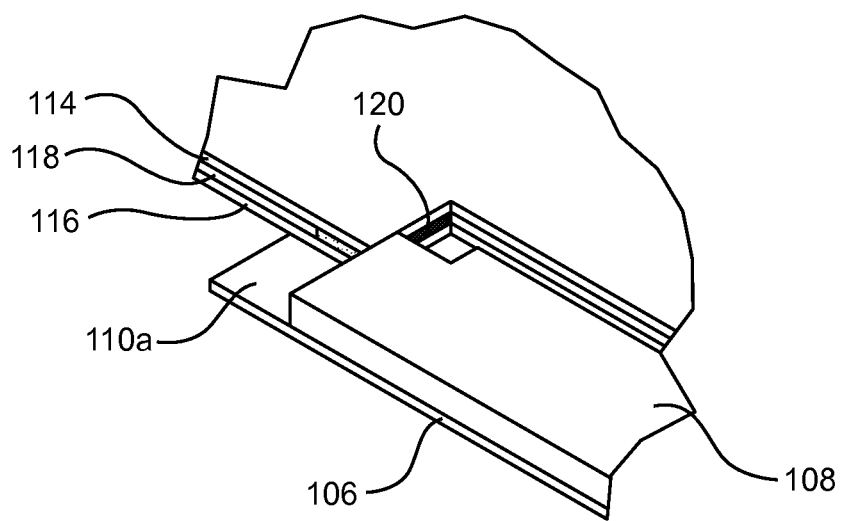

Analytical test strip 100 also has a determination portion 112 with a determination portion top layer 114, a determination portion bottom layer 116, and a patterned determination layer spacer layer 118 (see FIGS. 6A and 6B in particular). Determination portion 112 is configured such that determination chamber 120 is defined therein (see FIGS. 5, 6A and 6B in particular). In FIG. 6A only, determination chamber 120 (which is defined as a cavity) is depicted with cross-hatches for clarity.

Determination chamber 120 has at least one capillary dimension and is, therefore, considered capillary determination chamber. For example, in the embodiment and perspective of FIGS. 1-8, the dimensional height of the capillary determination chamber can be in the range of 0.025 mm to 0.18 mm.

Figure 7:
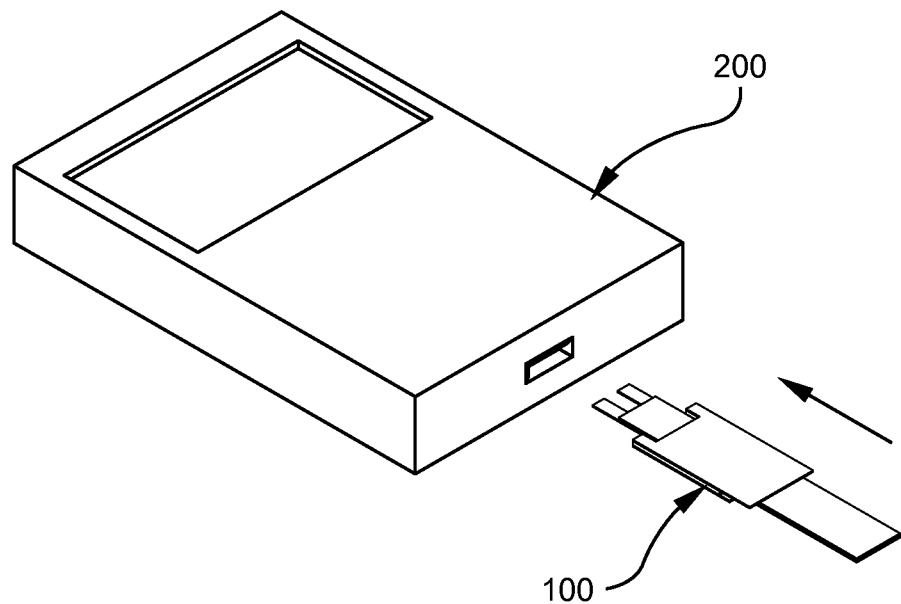
FIG. 7 is a simplified perspective depiction of the analytical test strip of FIG. 1 prior to insertion into a test meter, with the arrow depicting the direction of insertion, during a method according to an embodiment of the present invention.
Figure 8:
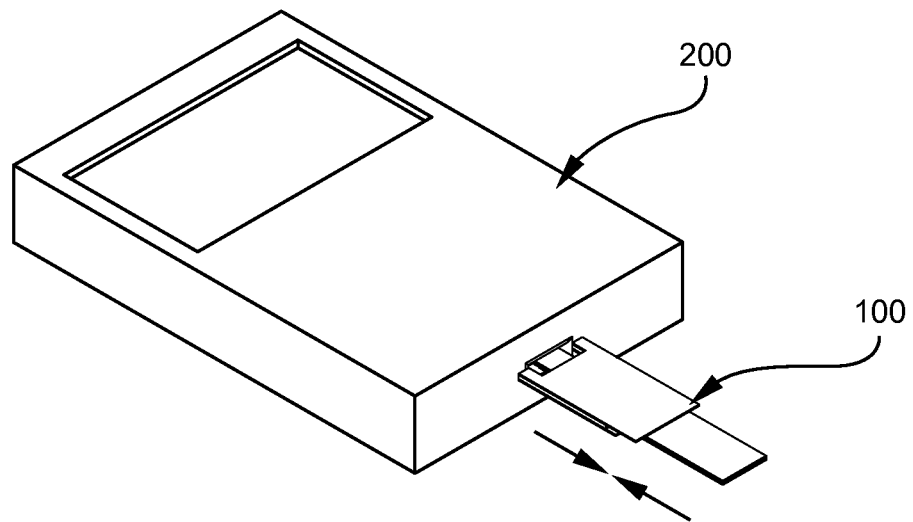
FIG. 8 is a simplified perspective depiction of the analytical test strip of FIG. 1 following insertion into a test meter, with the arrows depicting relative movement of a sample collection reservoir of the analytical test strip and a determination chamber of the analytical test strip with respect to one another, during a method according to an embodiment of the present invention.

Determination portion 112 also includes test meter electrical connectors 122a and 122b configured to operably connect electrodes (not depicted in the FIGs.) of the analytical test strip to test meter 200 (depicted in FIGS. 7 and 8).

Figure 2:
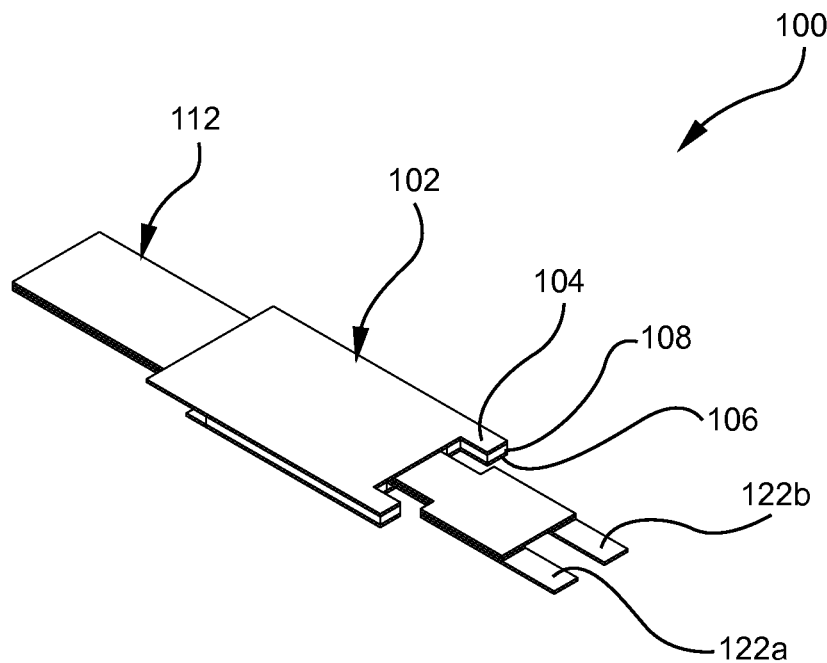
FIG. 2 is a simplified perspective view of the analytical test strip of FIG. 1 prior to insertion into a test meter (not depicted in FIG. 2) during a method according to an embodiment of the present invention.
Figure 3:
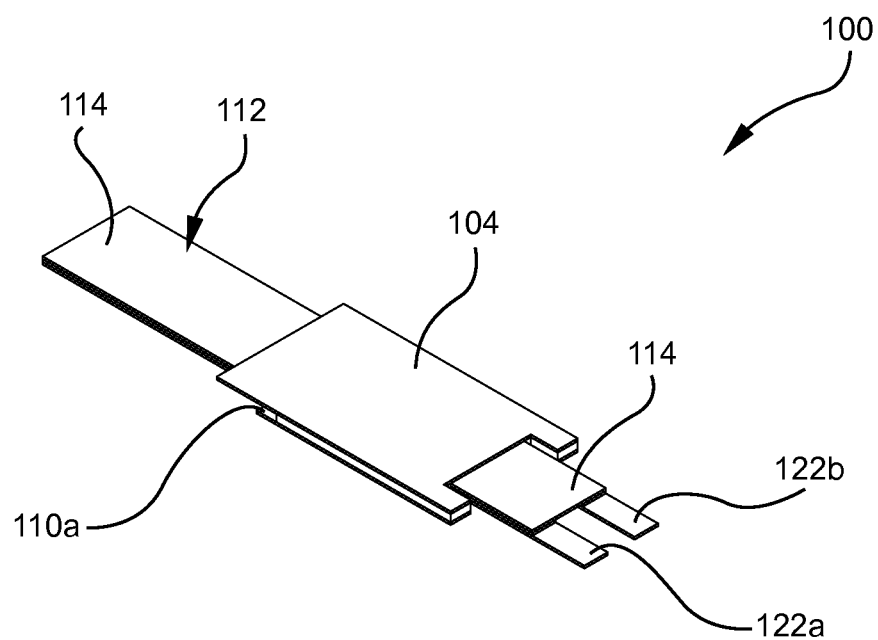
FIG. 3 is a simplified perspective view of the analytical test strip of FIG. 1 following insertion into a test meter (not depicted in FIG. 3) during a method according to an embodiment of the present invention.
Figure 4:
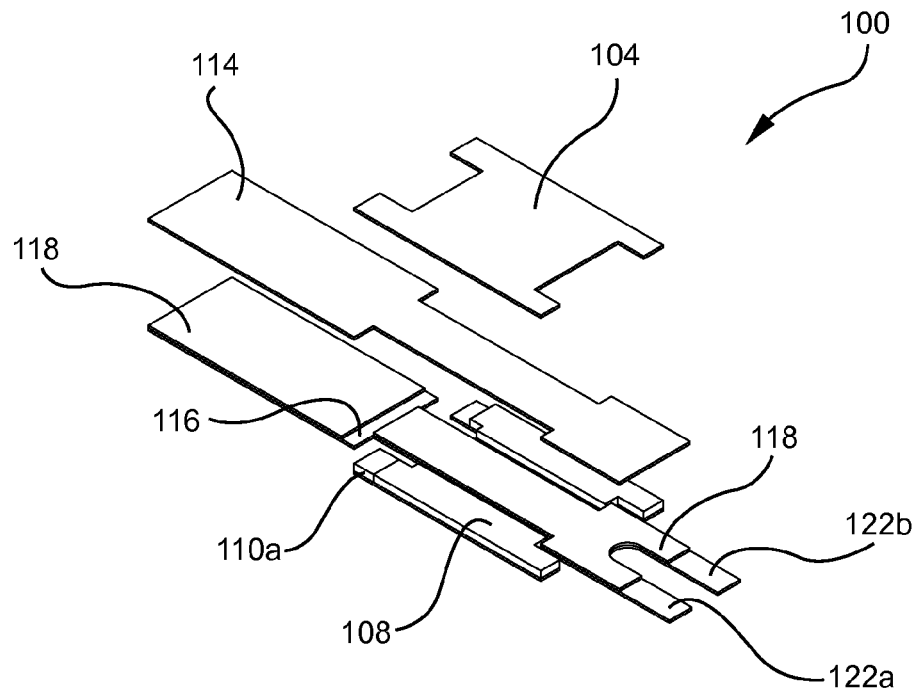
FIG. 4 is a simplified exploded view of the analytical test strip of FIG. 1 following application of a bodily fluid sample (depicted by the dotted area) to the sample collection reservoir thereof and prior to insertion into a test meter (not shown) during a method according to an embodiment of the present invention.
Figure 5:
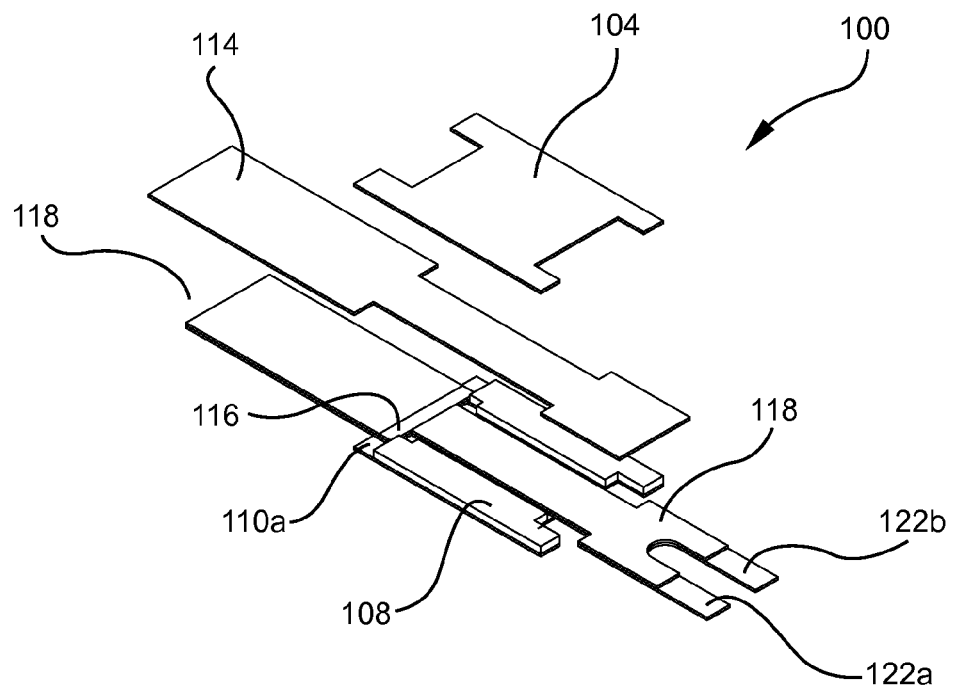
FIG. 5 is a simplified exploded view of the analytical test strip of FIG. 1 following application of a bodily fluid sample to the sample collection reservoir thereof and insertion into a test meter (not shown) such that at least a portion of the bodily fluid sample (again depicted by a dotted area) has been automatically transferred from the sample collection reservoir to the determination chamber during a method according to an embodiment of the present invention.

Sample collection portion 102 and determination portion 112 are configured such that dual sample collection reservoirs 110a and 110b are isolated from fluid communication with determination chamber 120 prior to insertion of analytical test strip 100 into test meter 200 (see, for example, FIGS. 2 and 4). However, sample collection portion 102 and determination portion 112 are also configured such that dual sample collection reservoir 110a and 110b are placed into fluid communication with determination chamber 120 and such that at least a portion of the bodily fluid sample is consequentially transferred from a sample collection reservoir to the determination chamber (see the bodily fluid transfer depicted in FIGS. 6A and 6B).

In the analytical test strip of FIGS. 1-8, the transfer of at least a portion of the bodily fluid sample occurs automatically via capillary action once fluidic communication between a sample collection reservoir and the determination chamber has been established. Analytical test strip 100 is also configured such that dual sample collection reservoirs 110a and 110b and the determination chamber 120 are moveable with respect to one another (compare, for example, FIGS. 1 and 3 and FIGS. 7 and 8) such that inserting analytical test strip into a test meter (such as meter 200 of FIGS. 7 and 8) establishes fluid communication between a sample collection reservoir that has had a bodily fluid sample applied thereto and determination chamber 120 by movement of the sample collection reservoir and determination chamber with respect to one another. Such movement can be, for example, a sliding movement of the sample collection reservoirs with respect to the determination chamber wherein the determination portion slides between the collection portion top layer and the collection portion bottom layer as depicted in, for example, FIGS. 2 and 3.

In analytical test strip 100, the height of the determination chamber is lower than the height of the sample collection reservoir (see FIG. 6B in particular). This height difference facilitates transfer of a bodily fluid sample from the sample collection reservoir to the determination chamber once fluid communication therebetween has been established by insertion of the analytical test strip into a test meter (as depicted in, for example, FIGS. 7 and 8). However, once apprised of the present disclosure, one skilled in the art will recognize that any suitable configuration of fluid communication between the sample collection reservoir and determination chamber that provides for the automatic transfer of the bodily fluid sample as a consequence of the test strip being inserted into a test meter can be employed.

Once apprised on the present disclosure, one skilled in the art will recognize that analytical test strips employed in embodiments of the present invention (including analytical test strip 100) will include suitable layers, reagents (e.g., enzymatic reagents) components (such as working, reference and counter electrodes) and features in addition to those depicted and described herein. For the sake of simplicity and clarity, such suitable layers, reagents, components and features are not depicted in the FIGs. nor fully described herein. However, conventional analytical test strips for the determination of an analyte in a bodily fluid sample are described in, for example, U.S. Pat. Nos. 5,708,247; 5,951,836; 6,241,862; and 6,284,125, each of which is hereby incorporated in full by reference.

Once apprised of the present disclosure, one skilled in the art will also recognize that test meter 200 includes suitable components for the determination of an analyte in a bodily sample applied to analytical test strip 100. For the sake of simplicity and clarity, such suitable components are not depicted in the FIGs. nor fully described herein. However, conventional hand-held test meters for the determination of an analyte in a bodily fluid sample are described in, for example, U.S. Pat. No. 7,468,125 and U.S. Patent Application Publication Nos. 2009/0301899 and 2007/0084734, each of which is hereby incorporated in full by reference.

Analytical test strips employed in methods according to embodiments of the present invention, including analytical test strip 100, can be manufactured using any suitable manufacturing technique including, for example, web-based manufacturing techniques that involve the lamination, punching, and coating, trimming and singulation of various layers to construct the analytical test strip. Moreover, the analytical test strips can be formed of any suitable materials known to one of skill in the art.

Figure 9:
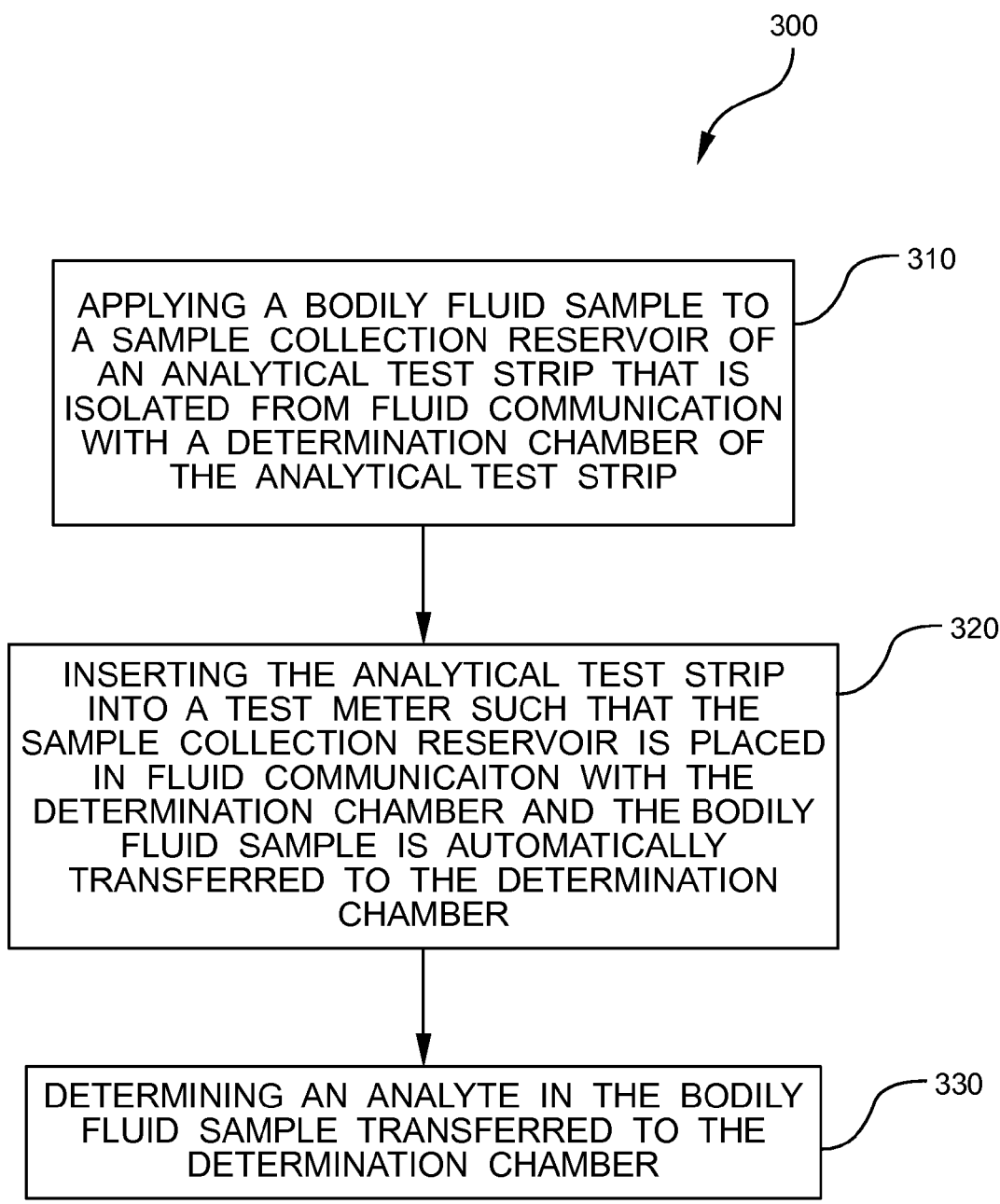
FIG. 9 is a flow diagram depicting stages in a method for employing a hand-held test meter according to an embodiment of the present invention.

FIG. 9 is a flow diagram depicting stages in a method 300 for transferring a bodily fluid sample (such as a whole blood sample) for determination of an analyte (for example glucose) therein according to an embodiment of the present invention. Method 300 includes applying the bodily fluid sample to a sample collection reservoir of an analytical test strip (see step 310 of FIG. 9).

The sample collection reservoir can be any suitable sample collection reservoir including, for example, a capillary sample collection reservoir such as those depicted in the analytical test strip of FIGS. 1-8. The analytical test strip can be, for example, the analytical test strip depicted in FIGS. 1-8.

During step 310 the sample collection reservoir is isolated from (i.e., separated from, cut off from, or detached from) fluid communication with a determination chamber of the analytical test strip. Such a determination chamber can be a reagent-containing electrode chamber configured for the electrochemical-based determination of the analyte in the bodily fluid sample.

Subsequently, at step 320, the analytical test strip is inserted into a test meter such that the sample collection reservoir is placed into fluid communication with the determination chamber and such that at least a portion of the bodily fluid sample is consequentially (automatically) transferred from the sample collection reservoir to the determination chamber. Such an insertion is depicted, in a non-limiting manner, in FIGS. 7 and 8 and the bodily fluid sample transfer is depicted, also in a non-limiting manner, in FIGS. 6A and 6B.

Method 300 also includes determining an analyte in the bodily fluid sample transferred to the determination chamber. Once apprised of the present disclosure, one skilled in the art will recognize that such a determination can employ the analytical test strip, test meter and a variety of analytical techniques that are well known in the art.

If desired, method 300 can include an additional step of pre-treating, following application of the bodily fluid sample and prior to the determining of the analyte, the applied bodily fluid sample in the sample collection reservoir. Such a pre-treatment can be any suitable chemical or enzymatic pretreatment including, for example, pretreatment with an anticoagulant compound, an enzymatic pretreatment that removes interfering substances (such as non-glucose interfering sugars or other reducing agents) from the bodily fluid sample or pre-treatment with enzymes such as uricase, ascorbate oxidase and/or xylose oxidase.

Moreover, once apprised of the present disclosure, one skilled in the art will recognize that methods according to embodiments of the present invention, including method 300, can be readily modified to incorporate any of the techniques, benefits and characteristics of the analytical test strips and test meters described herein. For example, the analytical test strip can be an electrochemical-based analytical test strip and the test meter can be a hand-held test meter.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A method for the transfer of a bodily fluid sample during the determination of an analyte in the bodily fluid sample, the method comprising:
    applying a bodily fluid sample to a sample collection reservoir of an analytical test strip, the sample collection reservoir being isolated from fluid communication with a determination chamber of the analytical test strip;
    inserting the analytical test strip into a test meter such that the sample collection reservoir is placed into fluid communication with the determination chamber and such that at least a portion of the bodily fluid sample is consequentially transferred from the sample collection reservoir to the determination chamber; and
    determining an analyte in the bodily fluid sample transferred to the determination chamber.

2. The method of claim 1 further comprising:
    pre-treating, following application of the bodily fluid sample and prior to the determining of the analyte, the applied bodily fluid sample in the sample collection reservoir.

3. The method of claim 2 wherein the pre-treating includes one of a chemical pre-treatment of the applied bodily fluid sample and an enzymatic pre-treatment of the applied bodily fluid sample.

4. The method of claim 1 wherein the sample collection reservoir is a capillary sample collection reservoir and the determination chamber is a capillary determination chamber.

5. The method of claim 4 wherein at least one dimension of the capillary sample chamber is in the range of 0.15 mm to 0.5 mm and one dimension of the capillary determination chamber is in the range of 0.025 mm to 0.18 mm.

6. The method of claim 5 wherein the inserting step is such that at least a portion of the bodily fluid sample is transferred from the capillary sample collection reservoir to the capillary determination chamber by capillary action upon insertion of the analytical test strip into the test meter.

7. The method of claim 1 wherein the analytical test strip is configured such that the sample collection reservoir and the determination chamber are moveable with respect to one another; and
    wherein the inserting step establishes fluid communication between the sample collection chamber and determination chamber by movement of the sample collection reservoir and determination chamber with respect to one another.

8. The method of claim 7 wherein the sample collection reservoir is slidable with respect to the determination chamber and wherein insertion of the analytical test strip into the test meter serves to slide the sample collection chamber such that the sample collection chamber is in fluid communication with the determination chamber.

9. The method of claim 1 wherein the analytical test strip is an electrochemical-based analytical test strip and includes at least one electrode in the determination chamber.

10. The method of claim 1 wherein the analytical test strip is configured to include dual sample collection reservoirs.

11. The method of claim 1 wherein the bodily fluid sample is a whole blood sample and the analyte is glucose.

\* \* \* \* \*